US012665061B2

(12) United States Patent　　(10) Patent No.:　US 12,665,061 B2
Addison et al.　　　　　　　　　(45) Date of Patent:　Jun. 23, 2026

(54) NOCICEPTION EVENT IDENTIFICATION BASED ON A RELATIVE CHANGE IN A NOCICEPTION PARAMETER

(71) Applicant: Covidien LP, Mansfield, MA (US)

(72) Inventors: Paul S. Addison, Edinburgh (GB); Dean Montgomery, Edinburgh (GB)

(73) Assignee: Covidien LP, Mansfield, MA (US)

( * ) Notice: Subject to any disclaimer, the term of this patent is extended or adjusted under 35 U.S.C. 154(b) by 356 days.

(21) Appl. No.: 18/249,524

(22) PCT Filed: Nov. 17, 2021

(86) PCT No.: PCT/US2021/059709
　　§ 371 (c)(1),
　　(2) Date: Apr. 18, 2023

(87) PCT Pub. No.: WO2022/109013
　　PCT Pub. Date: May 27, 2022

(65) Prior Publication Data
　　US 2023/0386635 A1　　Nov. 30, 2023

Related U.S. Application Data

(60) Provisional application No. 63/115,383, filed on Nov. 18, 2020.

(51) Int. Cl.
　　*G16H 20/10*　　　　(2018.01)
　　*A61B 5/00*　　　　(2006.01)
　　　　　　(Continued)
(52) U.S. Cl.
　　CPC ........... *G16H 20/10* (2018.01); *A61B 5/4821* (2013.01); *A61B 5/7475* (2013.01);
　　　　　　(Continued)

(58) Field of Classification Search
　　CPC .......... A61B 2017/0073; A61B 5/4821; A61B 5/4824; A61B 5/7475; A61B 5/4827;
　　　　　　(Continued)

(56) References Cited

U.S. PATENT DOCUMENTS 7,407,485 B2　8/2008　Huiku
7,407,486 B2　8/2008　Huiku et al.
　　　　　　(Continued)

FOREIGN PATENT DOCUMENTS

CN　　108376559 A　　8/2018
JP　　2010081950 A　　4/2010
　　　　　(Continued)

OTHER PUBLICATIONS

"Medasense—Nociception Level Detection", Medasense, Jan. 10, 2017, 34 pp.
　　　　　(Continued)

*Primary Examiner* — Amanda K Hulbert
(74) *Attorney, Agent, or Firm* — Dymera IP, LLC

(57) ABSTRACT

In some examples, a patient monitoring system includes processing circuitry configured to detect an occurrence of a nociception event of a patient during a medical procedure. The processing circuitry may, for example, determine, based at least in part on a nociception parameter of the patient in an interrogation window, a nociception parameter level, determine, based at least in part on the nociception parameter of the patient in a baseline window that corresponds to the interrogation window, a baseline nociception parameter level, determine a difference in nociception parameter levels between the baseline nociception parameter level and the nociception parameter level, detect, based at least in part on the difference in nociception parameter levels, an occurrence of a nociception event, and in response to detecting the
　　　　　　(Continued)

occurrence of the nociception event, provide an indication to adjust an amount of analgesic administered to the patient.

14 Claims, 5 Drawing Sheets

(51) Int. Cl.
| | | |
|---|---|---|
| *A61M 5/172* | (2006.01) | |
| *A61M 16/10* | (2006.01) | |

(52) U.S. Cl.
 CPC ........ *A61M 5/1723* (2013.01); *A61M 16/104* (2013.01); *A61M 2205/52* (2013.01)

(58) Field of Classification Search
 CPC ........ A61M 16/104; A61M 2021/0077; A61M 21/02; A61M 2202/0007; A61M 2202/0241; A61M 2202/048; A61M 2205/3306; A61M 2205/3375; A61M 2205/3553; A61M 2205/3584; A61M 2205/3592; A61M 2205/505; A61M 2205/52; A61M 2205/581; A61M 2205/582; A61M 2205/583; A61M 2209/088; A61M 2230/005; A61M 2230/04; A61M 2230/06; A61M 2230/10; A61M 2230/20; A61M 2230/205; A61M 2230/30; A61M 2230/42; A61M 2230/50; A61M 2230/60; A61M 2230/65; A61M 5/1723; A61P 23/00; G16H 20/10; G16H 50/20
 See application file for complete search history.

(56) References Cited

U.S. PATENT DOCUMENTS

| | | | |
|---|---|---|---|
| 8,463,370 | B2 | 6/2013 | Korhonen et al. |
| 8,574,156 | B2 | 11/2013 | Uutela et al. |
| 8,641,632 | B2 | 2/2014 | Quintin et al. |
| 8,862,238 | B2 | 10/2014 | Rahimi et al. |
| 9,326,725 | B2 | 5/2016 | Finkel et al. |
| 9,402,558 | B2 | 8/2016 | John et al. |
| 9,579,457 | B2 | 2/2017 | Osorio et al. |
| 9,861,317 | B2 | 1/2018 | Ochs |
| 10,285,597 | B2 | 5/2019 | Franz et al. |
| 10,388,405 | B2 | 8/2019 | Verghese |

| | | | |
|---|---|---|---|
| 2008/0242955 | A1 | 10/2008 | Uutela et al. |
| 2008/0319274 | A1 | 12/2008 | Ballegaard et al. |
| 2011/0082440 | A1 | 4/2011 | Kimmo et al. |
| 2011/0118619 | A1 | 5/2011 | Burton et al. |
| 2012/0226186 | A1 | 9/2012 | Baars et al. |
| 2013/0150748 | A1 | 6/2013 | Jensen |
| 2014/0276549 | A1 | 9/2014 | Osorio |
| 2015/0201879 | A1 | 7/2015 | Hargrove |
| 2018/0000409 | A1 | 1/2018 | Jensen et al. |
| 2018/0085055 | A1 | 3/2018 | Annoni et al. |
| 2018/0206784 | A1 | 7/2018 | Jensen et al. |
| 2018/0310877 | A1* | 11/2018 | Zuckerman Stark .. A61B 5/392 |
| 2022/0015696 | A1 | 1/2022 | Addison et al. |

FOREIGN PATENT DOCUMENTS

| | | | |
|---|---|---|---|
| WO | 2009063463 | A2 | 5/2009 |
| WO | 2013140106 | A1 | 9/2013 |
| WO | 2018019214 | A1 | 2/2018 |
| WO | 2019211335 | A1 | 11/2019 |

OTHER PUBLICATIONS

Chanques et al., "Analgesia nociception index for the assessment of pain in critically ill patients: a diagnostic accuracy study," British Journal of Anaesthesia, vol. 119, No. 4, Elsevier Ltd., Oct. 2017, pp. 812-820.

Funcke et al., "Guiding Opioid Administration by 3 Different Analgesia Nociception Monitoring Indices During General Anesthesia Alters Intraoperative Sufentanil Consumption and Stress Hormone Release: A Randomized Controlled Pilot Study", Anesthesia & Analgesia, May 20, 2020, pp. 1-9.

Hemmerling et al., "Robotic Anesthesia—A Vision for the Future of Anesthesia", Departments of Anesthesia, McGill University, Sep.-Dec. 2011, pp. 1-20.

International Preliminary Report on Patentability from International Application No. PCT/US2021/059709 dated Jun. 1, 2023, 9 pp.

International Search Report and Written Opinion of International Application No. PCT/US2021/059709 dated Feb. 25, 2022, 16 pp.

Julien-Marsollier et al., "Evaluation of the analgesia nociception index for monitoring intraoperative analgesia in children", British Journal of Anaesthesia, vol. 121, No. 2, Elsevier, Apr. 26, 2018, pp. 462-468, doi: 10.1016/j.bja.2018.03.034.

U.S. Appl. No. 18/249,945, filed Nov. 18, 2021, naming inventors Addison et al.

"European Communication pursuant to Article 94(3) EPC"; European Application No. 21 830 872.8-1113, Sep. 12, 2025, 9 pgs.

\* cited by examiner

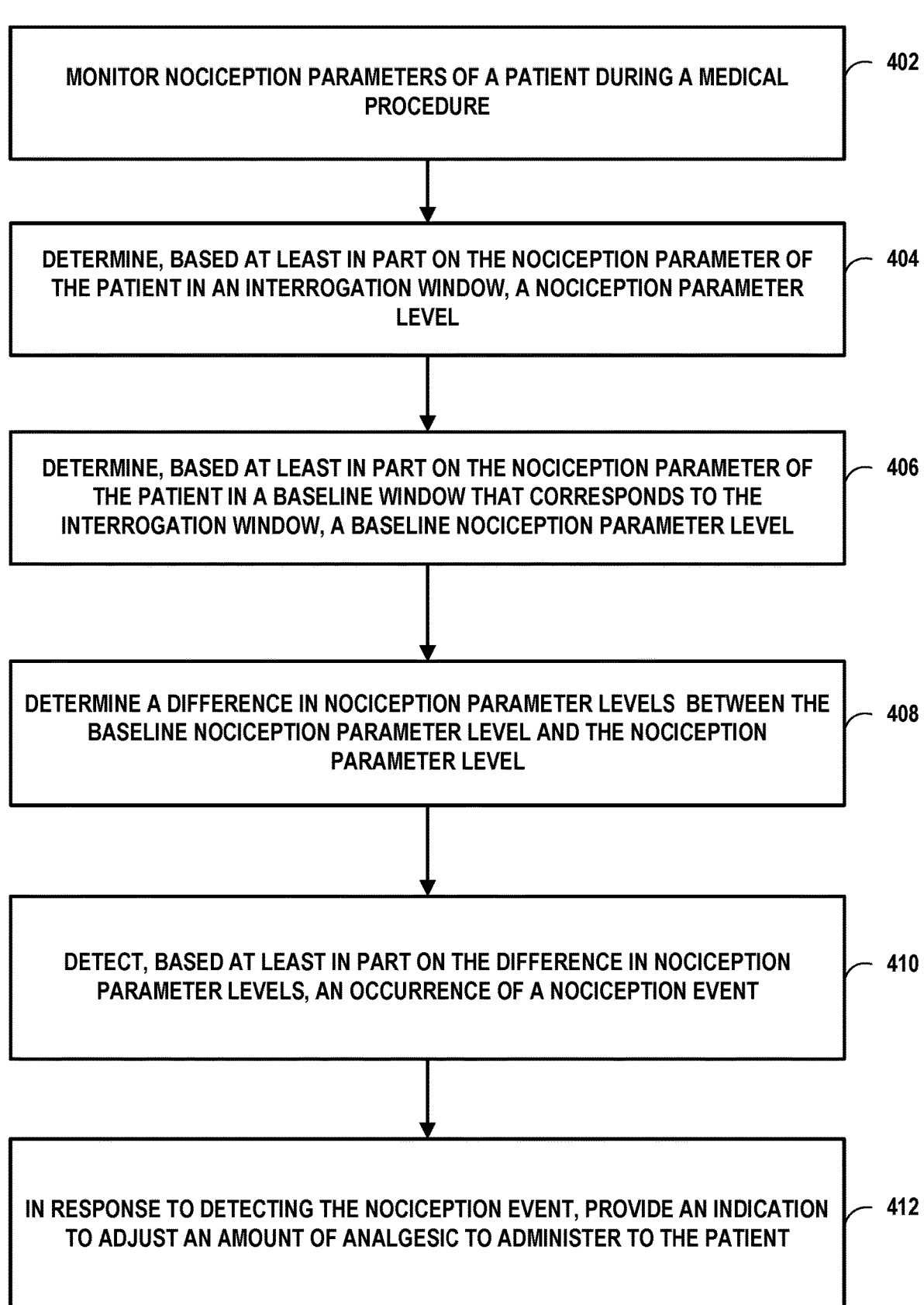

MONITOR NOCICEPTION PARAMETERS OF A PATIENT DURING A MEDICAL PROCEDURE — 402

DETERMINE, BASED AT LEAST IN PART ON THE NOCICEPTION PARAMETER OF THE PATIENT IN AN INTERROGATION WINDOW, A NOCICEPTION PARAMETER LEVEL — 404

DETERMINE, BASED AT LEAST IN PART ON THE NOCICEPTION PARAMETER OF THE PATIENT IN A BASELINE WINDOW THAT CORRESPONDS TO THE INTERROGATION WINDOW, A BASELINE NOCICEPTION PARAMETER LEVEL — 406

DETERMINE A DIFFERENCE IN NOCICEPTION PARAMETER LEVELS BETWEEN THE BASELINE NOCICEPTION PARAMETER LEVEL AND THE NOCICEPTION PARAMETER LEVEL — 408

DETECT, BASED AT LEAST IN PART ON THE DIFFERENCE IN NOCICEPTION PARAMETER LEVELS, AN OCCURRENCE OF A NOCICEPTION EVENT — 410

IN RESPONSE TO DETECTING THE NOCICEPTION EVENT, PROVIDE AN INDICATION TO ADJUST AN AMOUNT OF ANALGESIC TO ADMINISTER TO THE PATIENT — 412

FIG. 4

NOCICEPTION EVENT IDENTIFICATION BASED ON A RELATIVE CHANGE IN A NOCICEPTION PARAMETER

This application is a U.S. National Stage entry under 35 U.S.C. § 371 of International Application No. PCT/US2021/059709, filed Nov. 17, 2021, which claims priority from and the benefit of U.S. Provisional Patent Application No. 63/115,383, filed on Nov. 18, 2020, and entitled, "NOCICEPTION EVENT IDENTIFICATION BASED ON A RELATIVE CHANGE IN A NOCICEPTION PARAMETER," the entire content of each of which is incorporated herein by reference.

TECHNICAL FIELD

This disclosure relates to patient monitoring.

BACKGROUND

Nociception is a response of a sensory nervous system of a subject to certain stimuli, such as chemical, mechanical, or thermal stimuli, that causes the stimulation of sensory nerve cells called nociceptors.

SUMMARY

The present disclosure describes example devices, systems, and techniques for monitoring the nociception parameters of a patient undergoing a medical procedure based on one or more distinct changes in the nociception parameter over time. A clinician may use a nociception monitoring system to monitor the nociception parameters of the patient during a medical procedure to help determine the amount of analgesic to administer to the patient during the surgery.

In accordance with aspects of the present disclosure, a patient monitoring system may determine whether a patient is experiencing a severe nociceptive stimulus based on identifying distinct changes in the nociception parameter. For example, as the patient monitoring system monitors the nociception parameter of a patient during a medical procedure, the patient monitoring system may determine a nociception parameter level in an interrogation window and may compare the nociception parameter level with a baseline nociception parameter level from a baseline window to determine a difference in nociception parameter levels. If the difference in nociception parameter levels is greater than or equal to a threshold difference value, then the patient monitoring system may determine that there has been a distinct change in the nociception parameter of the patient that may require an increased amount of analgesic to be administered to the patient to dampen the nociception response of the patient.

In one example, a method includes monitoring, by processing circuitry, a nociception parameter of a patient during a medical procedure; determining, by the processing circuitry and based at least in part on the nociception parameter of the patient in an interrogation window, a nociception parameter level; determining, by the processing circuitry and based at least in part on the nociception parameter of the patient in a baseline window that corresponds to the interrogation window, a baseline nociception parameter level; determining, by the processing circuitry, a difference in nociception parameter levels between the baseline nociception parameter level and the nociception parameter level; detecting, by the processing circuitry and based at least in part on the difference in nociception parameter levels, an occurrence of a nociception event; and in response to detecting the occurrence of the nociception event, providing, by the processing circuitry, an indication to adjust an amount of analgesic administered to the patient.

In another example, a system includes: memory configured to store a nociception threshold; and processing circuitry communicably coupled to the memory and configured to: monitor a nociception parameter of a patient during a medical procedure; determine, based at least in part on the nociception parameter of the patient in an interrogation window, a nociception parameter level; determine, based at least in part on the nociception parameter of the patient in a baseline window that corresponds to the interrogation window, a baseline nociception parameter level; determine a difference in nociception parameter levels between the baseline nociception parameter level and the nociception parameter level; detect, based at least in part on the difference in nociception parameter levels, an occurrence of a nociception event; and in response to detecting the occurrence of the nociception event, provide an indication to adjust an amount of analgesic administered to the patient.

In another example, a non-transitory computer readable storage medium comprises instructions that, when executed, cause processing circuitry to: monitor a nociception parameter of a patient during a medical procedure; determine, based at least in part on the nociception parameter of the patient in an interrogation window, a nociception parameter level; determine, based at least in part on the nociception parameter of the patient in a baseline window that corresponds to the interrogation window, a baseline nociception parameter level; determine a difference in nociception parameter levels between the baseline nociception parameter level and the nociception parameter level; detect, based at least in part on the difference in nociception parameter levels, an occurrence of a nociception event; and in response to detecting the occurrence of the nociception event, provide an indication to adjust an amount of analgesic administered to the patient.

The details of one or more examples are set forth in the accompanying drawings and the description below. Other features, objects, and advantages will be apparent from the description and drawings, and from the claims.

BRIEF DESCRIPTION OF THE DRAWINGS

FIG. 4 is a flow diagram illustrating an example method of determining whether to increase the amount of analgesic administered to patient undergoing a medical procedure.

DETAILED DESCRIPTION

Figure 1:
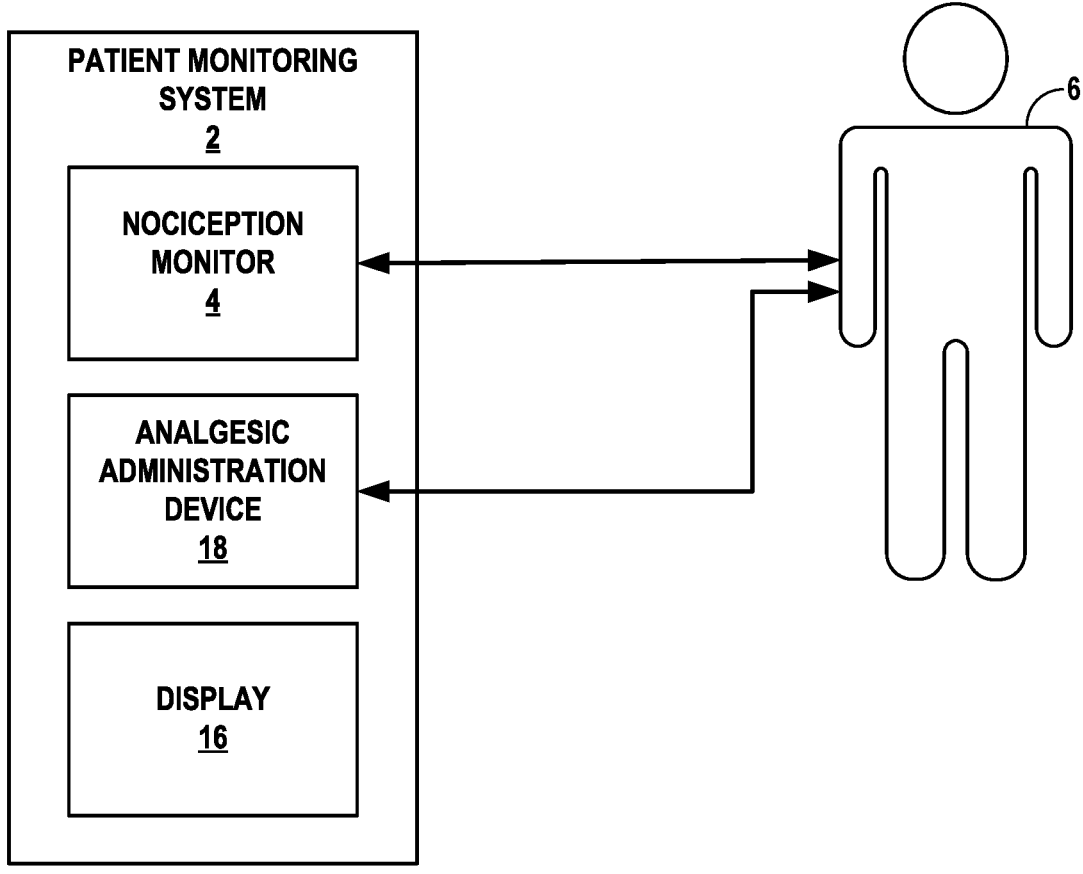
FIG. 1 is a block diagram illustrating an example environment in which a patient monitoring system monitors one or more nociception parameters of a patient undergoing a medical procedure.

Aspects of the present disclosure describe devices, systems, and techniques for monitoring a nociception parameter of a patient undergoing a medical procedure, such as surgery, to help determine the amount of analgesic to administer to the patient during the medical procedure. In some examples, a patient monitoring system, also referred to herein as a nociception monitor, may provide a continuous measure of a nociception parameter for a patient undergoing a medical procedure in order to track the nociception response of the patient. The nociception parameter can be based on one or more sensed physiological signals, such as an electrocardiogram (ECG), a photoplethysmogram (PPG), electroencephalogram (EEG), skin conductance, body temperature, and the like, and may typically be displayed over time. A clinician may monitor the nociception parameter of a patient to determine the amount of analgesic to administer to the patient during the medical procedure. As the patient undergoes the medical procedure, the clinician may administer analgesic to the patient to reduce stress experienced by the patient during the medical procedure. While this stress is generally referred to herein as "surgical stress," the stress may be the result of one or more events occurring during any medical procedure and is not limited to surgery-induced stress responses of a patient. The stress can be, for example, an activation of a patient's sympathetic nervous system, an endocrine response, and/or immunological or hematological change in the patient. Example nociception parameters include nociception level index (NOL), analgesia nociception index (ANI), surgical pleth index (SPI), composite variability index (CVI), and the like.

A clinician may use a nociception monitoring system to monitor the nociception parameter of the patient, which may correspond to the amount of surgical stress experienced by the patient, during the medical procedure, and the clinician may determine whether to adjust the amount of analgesic to administer to the patient based on the nociception parameter of the patient. In some examples, the clinician may monitor the nociception parameter of the patient to determine whether the nociception parameter of the patient increases above a nociception threshold, which may indicate a severe nociceptive stimulus experienced by the patient. The clinician may, in response to the nociception parameter of the patient increasing above the nociception threshold, adjust (e.g., increase) the amount of analgesic to dampen the nociception stimulus experienced by the patient.

Noise in the nociception parameters may occasionally cause false positive indications of a severe nociceptive stimulus. Such noise may be caused by patient motion, electrocautery, administration of drugs to the patient, and the like, or may be present in underlying signals from which the nociception parameters are derived. For example, such noise may cause the nociception monitoring system to sense increases in the nociception parameters of the patient above the nociception threshold even when there is not a corresponding increase in the surgical stress experienced by the patient. If the clinician were to increase the amount of analgesic administered to the patient in response to such false positive indications of a severe nociceptive stimulus, the clinician may unwittingly administer additional analgesic to the patient where it may not be required. In addition, different patients may respond differently to surgical stress and stimuli, such that the same level of nociception parameters of different patients may indicate different levels of surgical stress experienced by different patients. These different responses may be due to the physiology of patients, the amount of analgesic already administered to the patients, and the like.

Further, only using a nociception threshold for determining whether the patient is suffering a severe nociceptive stimulus may cause the patient monitoring systems to miss instances where there is a distinct change in the nociception parameter of the patient that may indicate that the patient is experiencing a severe nociceptive stimulus. For example, if the distinct change in the nociception parameter of the patient is a distinct rise in the nociception parameter that peaks below the nociception threshold, then the distinct change in the nociception parameter may nevertheless indicate that the patient is experiencing a severe nociceptive stimulus that may require an increased amount of analgesic to be administered to the patient to dampen down the nociception response.

This disclosure describes devices, systems, and methods for adaptively determining whether to adjust the amount of analgesic to administer to the patient based on the nociception parameter of the patient in ways that enable clinicians to more accurately adjust the amount of analgesic administered to the patients. Specifically, aspects of this disclosure describe techniques for a nociception monitoring system to monitor the nociception parameter of a patient and to detect distinct changes in the nociception parameter of the patient over time, such as a distinct increase in the nociception parameter of the patient over time or a distinct decrease in the nociception parameter of the patient over time. The nociception monitoring system may compare the level of the nociception parameter of the patient during the period of distinct change in the nociception parameter of the patient to a baseline nociception parameter level (e.g., determined at some point prior to the distinct change in the nociception parameter of the patient). If the difference between the level of the nociception parameter of the patient during the period of distinct change in the nociception parameter of the patient and the baseline nociception parameter level is greater than or equal to a threshold value, then the nociception monitoring system may determine that the patient is experiencing a severe nociceptive stimulus (e.g., referred to herein as a nociception event) and may generate an output that is indicative of the detected nociception event. The output may, for example, indicate that a clinician should increase the amount of analgesic administered to the patient.

By comparing the level of the nociception parameter of the patient during the period of distinct change in the nociception parameter of the patient with the baseline nociception parameter level, the devices, systems, and techniques of this disclosure may more accurately associate nociception parameters of a patient with actual increases in the surgical stress experienced by the patient. The accuracy may be increased, e.g., relative to examples in a system detects a nociception event (e.g., indicating a patient is experiencing a severe surgical stimulus) based on only a comparison of a nociception parameter to a nociception threshold value. Increasing the accuracy of the nociception monitoring system in this manner, e.g., increasing the accuracy with which the system detects a nociception event and generates an output indicative of the nociception event, may lead to positive outcomes for the patient by at least enabling a clinician or an analgesic administration system to more accurately and timely administer analgesic to the patient when it may be required to reduce the surgical stress caused to the patient and to decrease unnecessary administration of additional analgesic administered to the patient due to false positives.

FIG. 1 is a block diagram illustrating an example environment in which a patient monitoring system monitors one or more nociception parameters of a patient undergoing a medical procedure. As shown in FIG. 1, patient monitoring system 2 may monitor one or more physiological signals of patient 6 to determine the amount of surgical stress caused by the surgery to patient 6. By monitoring the amount of surgical stress experienced by patient 6, patient monitoring system 2 or a clinician that uses patient monitoring system 2 may be able to determine whether to increase the amount of analgesic to administer to the patient during the surgery.

Patient monitoring system 2 is configured to monitor patient 6 during a medical procedure, such as surgery, and configured to titrate analgesic or anesthetic delivered to patient 6 during surgery to provide anesthesia for patient 6. Patient monitoring system 2 may include nociception monitor 4, analgesic administration device 18, and display 16. As the clinician performs a medical procedure on patient 6, nociception monitor 4 of patient monitoring system 2 may monitor the amount of surgical stress experienced by patient 6 by monitoring one or more physiological signals of patient 6, such as, but not limited to one or more of an ECG, a PPG, an EEG, the skin conductance of patient 6, the body temperature of patient 6, a respiratory rate, and the like, to determine a measure of a nociception parameter associated with patient 6 during the surgery, where the nociception parameter corresponds to the amount of surgical stress experienced by patient 6. In some examples, the measure of the nociception parameter is continuously measured by system 2. In some examples, the nociception parameter may be an integer, and may range from, for example, 0 to 100. As such, by determining a continuous measure of a nociception parameter associated with patient 6 during the surgery, nociception monitor 4 may determine a continuous measure of the amount of surgical stress experienced by patient 6 during surgery.

Display 16 is configured to display the nociception parameter over time. For example, as nociception monitor 4 determines the nociception parameter associated with patient 6, display 16 may output a graphical representation of the nociception parameter over time, which may be viewed by a clinician to monitor the amount of surgical stress experienced by patient 6.

In some examples, patient monitoring system 2 includes analgesic administration device 18, which may include one or more components and/or devices configured to administer analgesic to patient 6 during surgery. Analgesic administration device 18 may be coupled to patient 6, such as via one or more intravenous (IV) lines, a breathing mask, a tube, and the like, to titrate analgesic to patient 6 in order to provide analgesia to patient 6 during surgery.

In some examples, the analgesic administration device 18 is configured to administer analgesic to patient 6 without user intervention from, for example, a clinician. That is, patient monitoring system 2 may control the amount of analgesic being administered by analgesic administration device 18 to patient 6 (i.e., automatically titrate analgesic delivered to patient 6), such as by increasing the amount of analgesic administered by analgesic administration device 18 to patient 6 and/or by decreasing the amount of analgesic administered by analgesic administration device 18 to patient 6, without user intervention.

In addition to or instead of an automatic administration of analgesia by analgesic administration device 18, in some examples, a clinician may control the amount of analgesic being administered by analgesic administration device 18 to patient 6. For example, the clinician may provide user input to patient monitoring system 2 indicative of the amount of analgesic to be administered by analgesic administration device 18 to patient 6. Patient monitoring system 2 may receive such user input indicative of the amount of analgesic being administered by analgesic administration device 18 to patient 6 and may, in response, control analgesic administration device 18 to administer the amount of analgesic to patient 6 indicated by the user input.

As a medical procedure is performed on patient 6, nociception monitor 4 of patient monitoring system 2 may continuously or periodically determine the nociception parameter associated with patient 6 in order to monitor the amount of surgical stress experienced by patient 6. In some examples, nociception monitor 4 may specify a nociception threshold for patient 6, where nociception parameters of patient 6 that are at or above the nociception threshold may be indicative of patient 6 experiencing a severe nociceptive stimulus (referred to herein as a nociception event). In the example where the nociception parameter of patient 6 may range from 0 to 100, a nociception threshold may also be an integer value between 0 and 100, such as 70, 80, and the like. The nociception threshold may be preset and may be the same for all patients, or may be adjusted, e.g., by a clinician, to a value that may be different for different patient.

As such, in some examples, if nociception monitor 4 determines that the nociception parameter of patient 6 is greater than or equal to the nociception threshold, then processing circuitry (not shown) of patient monitoring system 2 may detect a nociception event and may accordingly cause analgesic administration device 18 to increase the amount of analgesic administered to patient 6 to dampen down the surgical stress experienced by patient 6 and to decrease the nociception parameter of patient 6 to below the nociception threshold. In other examples, if nociception monitor 4 determines that the nociception parameter of patient 6 is greater than or equal to the nociception threshold, then processing circuitry of patient monitoring system 2 may provide an indication via display 16 or another user output device (e.g., audio circuitry configured to generate an audible output or circuitry configured to generate a tactile output perceived by a clinician) to indicate to adjust an amount of analgesic administered to patient 6.

In some examples, a clinician may determine a patient-specific nociception threshold based on making a tradeoff between the amount of surgical stress endured by patient 6 and the amount of analgesic administered to patient 6. For example, setting a higher nociception threshold may lead to relatively less analgesic being administered to patient 6, thereby leading patient 6 to endure relatively more surgical stress. On the other hand, setting a lower nociception threshold may lead to relatively more analgesic being administered to patient 6, thereby leading patient 6 to endure relatively less surgical stress.

In some examples, setting the nociception threshold too high may lead to underdosing patient 6 with analgesia, thereby causing the patient 6 to experience too much surgical stress, which may lead to poorer outcomes. In some examples, setting the nociception threshold too low may lead to overdosing patient 6 with analgesia, which may lead to patient 6 developing hyperalgesia after the medical procedure. Thus, if patient 6 is more susceptible to hyperalgesia, the clinician may choose to set a relatively higher nociception threshold for patient 6 to decrease the possibility of patient 6 developing hyperalgesia after the medical procedure.

In some examples, a clinician may determine an upper nociception threshold and a lower nociception threshold for patient 6, where the nociception parameter being greater than or equal to the upper nociception threshold may be indicative of underdosing patient 6 with analgesia, and where the nociception parameter being less than or equal to the lower nociception threshold may be indicative of overdosing patient 6 with analgesia. In these examples, when processing circuitry of patient monitoring system 6 determines that the nociception parameter is greater than or equal to the upper nociception threshold, processing circuitry of patient monitoring system 2 may detect a nociception event and may accordingly cause analgesic administration device 18 to increase the amount of analgesic administered to patient 6 to dampen down the surgical stress experienced by patient 6 and to decrease the nociception parameter of patient 6 to below the upper nociception threshold. Conversely, when processing circuitry of patient monitoring system 6 determines that the nociception parameter is less than or equal to the lower nociception threshold, processing circuitry of patient monitoring system 2 may detect a nociception event and may accordingly cause analgesic administration device 18 to decrease the amount of analgesic administered to patient 6 to stop overdosing of patient 6 and to increase the nociception parameter of patient 6 to above the lower nociception threshold.

In some examples, processing circuitry of patient monitoring system 2 may determine regions of interest in nociception parameter 32 as regions that correspond to distinct changes in nociception parameter 32 over time, such as a distinct rise in nociception parameter 32 over time or a distinct dip in nociception parameter 32.

In some examples, to provide additional information regarding patient 6 to a clinician, processing circuitry of patient monitoring system 2 is configured to determine one or more regions of interest in the nociception parameter of patient 6 monitored by nociception monitor 4 and may output indications of one or more regions of interest in the nociception parameter. For example, processing circuitry of patient monitoring system 2 may output, for display at display 16, indications of the one or more regions of interest in the nociception parameter. In other examples, processing circuitry of patient monitoring system 2 may output audible alerts, haptic feedback, and the like that are indicative of one or more regions of interest in the nociception parameter. Clinicians may be able to view, hear, or otherwise be made aware of the indications of the one or more regions of interest in the nociception parameter outputted by patient monitoring system to determine whether to adjust the amount of analgesic administered to patient 6 and/or determine how much to adjust the amount of analgesic administered to patient 6.

FIGS. 2A-2D illustrate an example techniques for determining one or more regions of interest in a nociception parameter, in accordance with aspects of this disclosure. When processing circuitry of patient monitoring system 2 determines a region of interest in the nociception parameter of patient 6, processing circuitry of patient monitoring system 2 may output an indication of the region of interest, such as for display at display 16. In some examples, as described in further detail below, processing circuitry of patient monitoring system 2 may also utilize the determined regions of interest in the nociception parameter to determine whether to adjust the amount of analgesic administered to patient 6 and/or determine how much to adjust the amount of analgesic administered to patient 6.

Figure 2A:
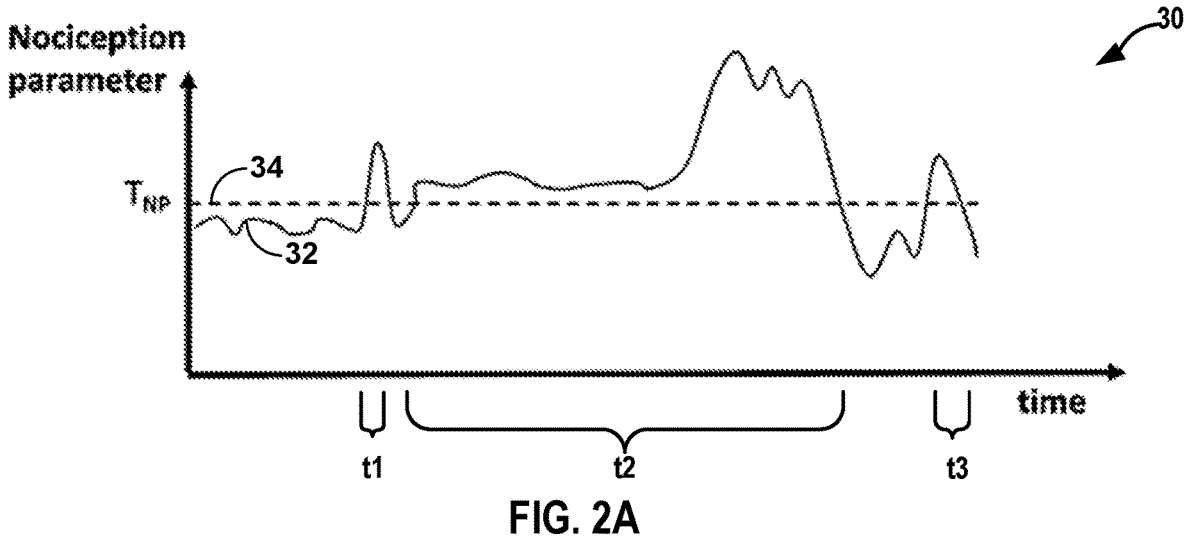
FIGS. 2A-2D illustrate an example techniques for determining one or more regions of interest in a nociception parameter, in accordance with aspects of this disclosure.

As shown in FIG. 2A, time graph 30 is a visual representation of the nociception parameter 32 of patient 6 over time during a medical procedure, such as monitored by nociception monitor 4. In the example of FIG. 2A, nociception parameter 32 may be greater than or equal to nociception threshold 34 during time periods t1, t2, and t3. In some examples, nociception threshold 34 may be predetermined or may be patient-specific. For example, processing circuitry of patient monitoring system 2 may be able to determine when an intubation event occurs and may adaptively determine a patient-specific nociception threshold for patient 6 based on the nociception response of patient 6 during the intubation event.

A distinct change in nociception parameter 32 over time may be a specified rate of increase in value of nociception parameter 32 over time or a specified rate of decrease in value of nociception parameter over time that is greater than or equal to a threshold rate of increase or a threshold rate of decrease. Examples of the period of time over which the increase or decrease in the value of nociception parameter 32 are measured to determine the rate of increase or decrease in the value of nociception parameter 32 may be 30 seconds, 1 minutes, 5 minutes, 10 minutes, and the like. The threshold rate of increase or decrease can be predetermined and stored by memory 41 (FIG. 3) of processing circuitry of patient monitoring system 2 or a memory separate from system 2, but accessible by system 2. In some examples, the threshold rate of increase or decrease is selected to correspond to an increase or a decrease, respectively, in a nociception parameter that is believed to correspond to a nociception event, e.g., the start or end of a nociception event.

Figure 2B:
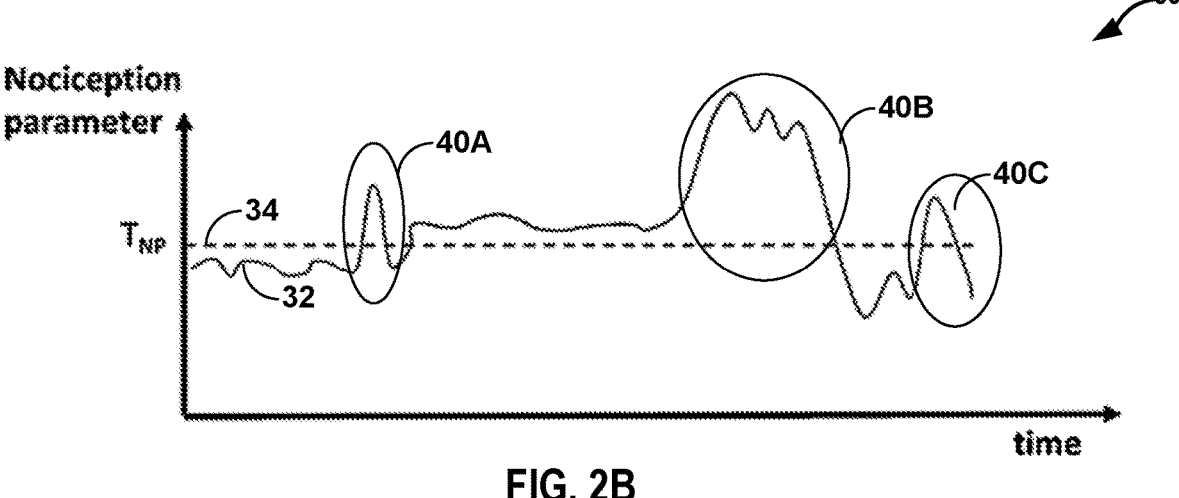

As shown in FIG. 2B, there may be a distinct change in nociception parameter 32 in regions 40A-40C because the rate of increase of nociception parameter 32 over time in regions 40A-40C may be greater than a threshold rate of increase. Thus, in some examples, processing circuitry of patient monitoring system 2 may determine regions 40A-40C to be regions of interest in nociception parameter 32. Note that even though the region of nociception parameter 32 between region 40A and region 40B is above nociception threshold 34, the region of nociception parameter 32 between region 40A and region 40B may not be a region of interest because the region does not correspond to a distinct change in nociception parameter 32. Instead, the value of nociception parameter 32 remains relatively stable in the region.

In some examples, processing circuitry of patient monitoring system 2 may determine the regions of interest to be regions in nociception parameter 32 that correspond to the leading edges (e.g., leading upslope or leading downslope) of the distinct changes in nociception parameter 32. A leading edge may begin at the start of the distinct change in nociception parameter 32 and may end at the peak value in the distinct change in nociception parameter 32. Thus, processing circuitry of patient monitoring system 2 may identify one or more regions in the nociception parameter that each encompasses a leading edge of a distinct rise or a distinct dip in the nociception parameter 32 over time and may therefore determine one or more regions of interest in nociception parameter 32 that corresponds to those one or more regions.

Figure 2C:
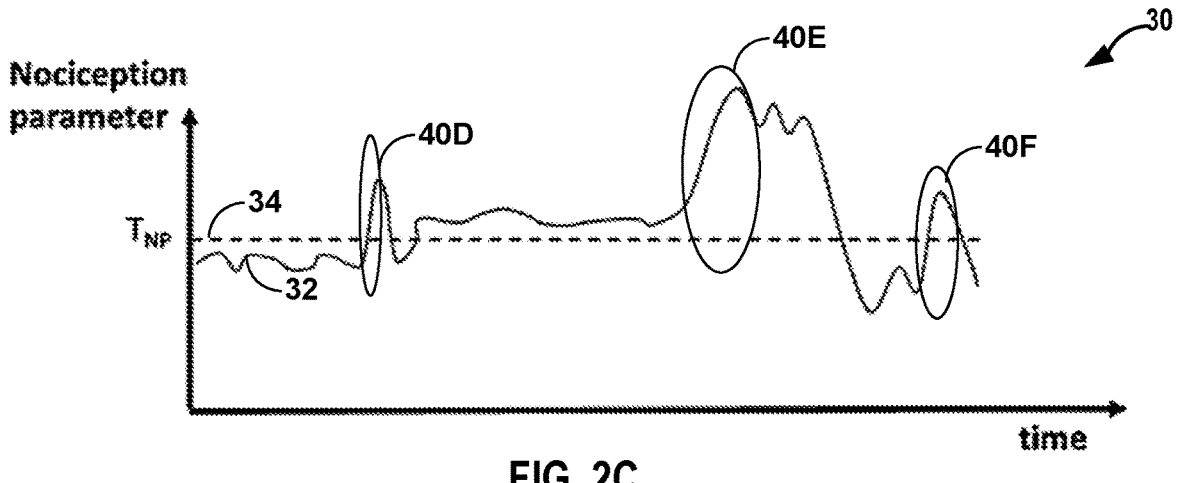

As shown in FIG. 2C, regions 40D-40F may each correspond to a leading edge of a distinct change in nociception parameter 32. As such, processing circuitry of patient monitoring system 2 may determine that regions 40D-40F corresponds to regions of interest in nociception parameter 32.

In some examples, processing circuitry of patient monitoring system 2 may determine the regions of interest to be regions in nociception parameter 32 that encompass the initial distinct change from an initial value until nociception parameter 32 returns to the initial value. That is, processing circuitry of patient monitoring system 2 may identify one or more regions in the nociception parameter 32 that each encompasses either one or more distinct rises or one or more distinct dips in the nociception parameter 32 over time from an initial value of the nociception parameter 32 until a return from the distinct rise or distinct dip in the nociception parameter 32 to the initial value. Processing circuitry of patient monitoring system 2 may therefore determine one or more regions of interest in nociception parameter 32 that corresponds to those one or more regions.

Figure 2D:
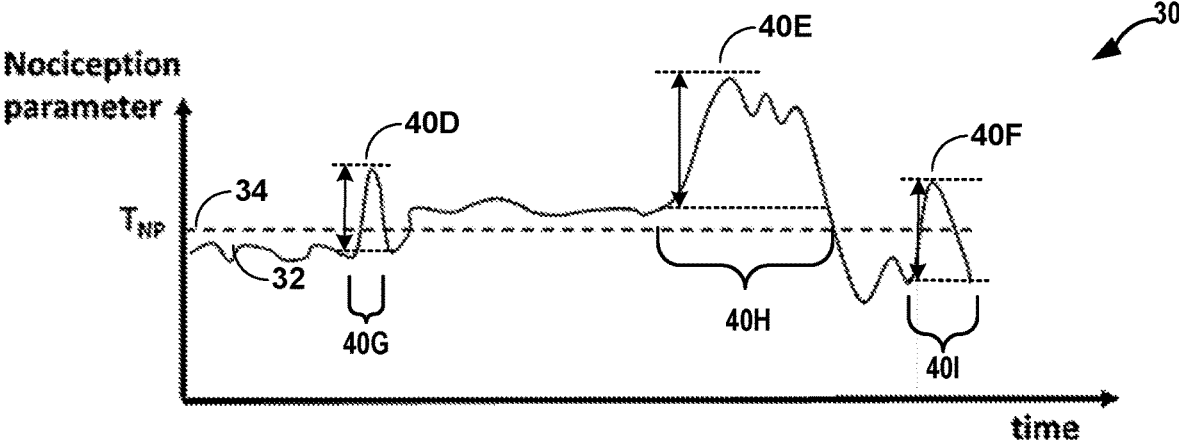

As shown in FIG. 2D, regions 40F-40H of nociception parameter 32 may each correspond to a region of nociception parameter 32 having a distinct rise from an initial value until nociception parameter 32 returns to the initial value. As such, processing circuitry of patient monitoring system 2 may determine that regions 40F-40H correspond to regions of interest in nociception parameter 32.

In some examples, in addition to determining one or more regions of interest in nociception parameter 32 of patient 6 based on a distinct change in nociception parameter 32, processing circuitry of patient monitoring system 2 may detect, based on the distinct changes in nociception parameter 32 of patient 6, an occurrence of a nociception event. Processing circuitry of patient monitoring system 2 may determine a difference between a characteristic value before and after the distinct change in nociception parameter 32 and may determine, based at least in part on the difference in the characteristic values, determine whether a nociception event has occurred.

Processing circuitry of patient monitoring system 2 may determine the characteristic values based on the values of nociception parameter 32. For example, as nociception monitor 4 continues to monitor nociception parameter 32 of patient 6, processing circuitry of patient monitoring system 2 may determine a baseline nociception parameter level. As nociception monitor 4 monitors nociception parameter 32 of patient 6, processing circuitry of patient monitoring system 2 may compare a nociception parameter level of nociception parameter 32, such as the current nociception parameter level of nociception parameter 32, to the baseline nociception parameter level to determine a difference in nociception parameter levels between the level of nociception parameter 32 with the baseline nociception parameter level. Processing circuitry of patient monitoring system 2 may therefore determine, based at least in part on the difference in nociception parameter levels, determine whether a nociception event has occurred.

Figure 2E:
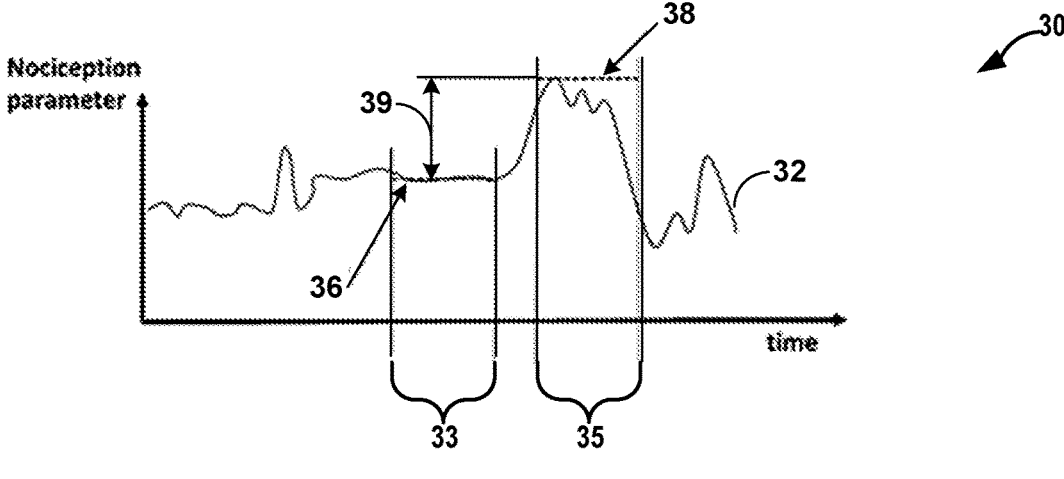
FIGS. 2E and 2F illustrate example techniques for detecting an occurrence of a nociception event based on the distinct changes in nociception parameter of the patient, in accordance with aspects of this disclosure.
Figure 2F:
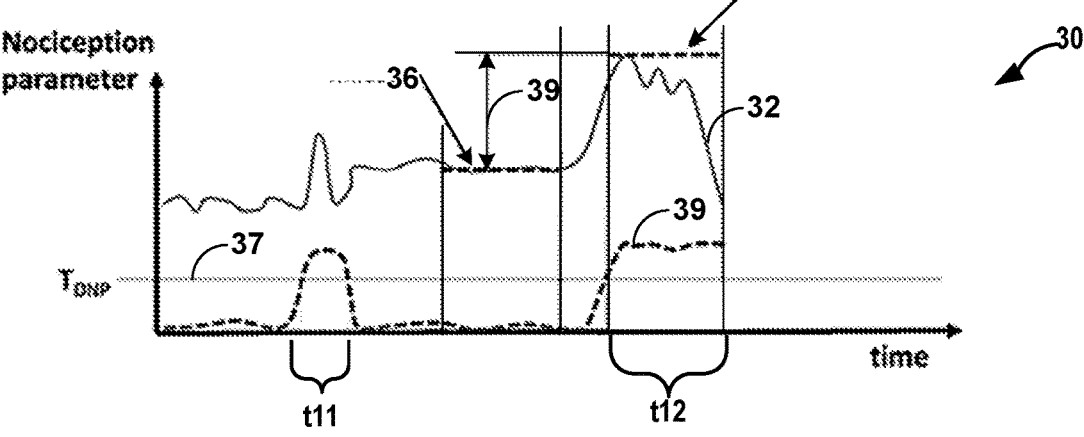

FIGS. 2E and 2F illustrate example techniques for detecting an occurrence of a nociception event based on the distinct changes in nociception parameter of the patient, in accordance with aspects of this disclosure. As shown in FIG. 2E, processing circuitry of patient monitoring system 2 may, for a nociception parameter level 38, determine the baseline nociception parameter level 36 based on the values of the nociception parameter 32 within a baseline window 33 of nociception parameter 32.

Nociception parameter level 38 may be a value of nociception parameter 32 within interrogation window 35 of nociception parameter 32, where interrogation window 35 may be a region of nociception parameter 32. In some examples, nociception parameter level 38 may be a maximum nociception parameter value (e.g., a peak nociception parameter value), a minimum nociception parameter value, a percentile nociception parameter value (e.g., $70^{th}$ percentile, $80^{th}$ percentile, etc.) of values of the nociception parameter 32 within the interrogation window 35, a median nociception parameter value, a mean nociception parameter value, or the like.

Baseline window 33 of nociception parameter 32 that corresponds to interrogation window 35 may be a region of nociception parameter 32 prior in time to interrogation window 35, where baseline window 33 does not overlap interrogation window 35. In other examples, baseline window 33 may partially overlap with interrogation window 35, but the start of baseline window 33 is prior in time to interrogation window 35. In some examples, baseline nociception parameter level 36 may be an average (e.g., mean, median etc.) of values of the nociception parameter 32 within the baseline window 33, a weighted average of values of the nociception parameter 32 within the baseline window 33, and the like.

In some examples, baseline window 33 may be of a fixed duration, such as 10 seconds, 20 seconds, 30 seconds, 40 seconds, 50 seconds, 60 seconds, 2 minutes, or the like. In some examples, interrogation window 35 may be of the same duration as baseline window 33, or may be of a different duration, such as 10 seconds, 20 seconds, 30 seconds, 40 seconds, 50 seconds, 60 seconds, 2 minutes, and the like.

In some examples, baseline window 33 may end immediately prior to or at the same time as the start of interrogation window 35. Thus, for example, a 30-second baseline window 33 may start 30 seconds before the start of interrogation window 35. In other examples, baseline window 33 may end a specified amount of time prior to the start of interrogation window 35. For example, baseline window 33 may end 10 seconds, 20 seconds, and the like prior to the start of interrogation window 35. Thus, in the example where baseline window 33 ends 10 seconds before the start of interrogation window 35, a 30 second baseline window 33 may start 40 seconds before the start of interrogation window 35.

Processing circuitry of patient monitoring system 2 may determine, a difference 39 in nociception parameter levels between baseline nociception parameter level 36 and nociception parameter level 38. In some examples, the difference 39 in nociception parameter levels may be nociception parameter level 38 subtracted from baseline nociception parameter level 36 or baseline nociception parameter level 36 subtracted from nociception parameter level 38. In some examples, the difference 39 in nociception parameter levels between baseline nociception parameter level 36 and nociception parameter level 38 may be an absolute difference between baseline nociception parameter level 36 and nociception parameter level 38, which may be the result of taking the absolute value of the result of subtracting baseline nociception parameter level 36 from nociception parameter level 38.

In some examples, the difference 39 in nociception parameter levels between baseline nociception parameter level 36 and nociception parameter level 38 may be a percentage difference, which may be the percentage difference between baseline nociception parameter level 36 and nociception parameter level 38. For example, if baseline nociception parameter level 36 has a value of 40, and if nociception parameter level 38 has a value of 50, then the percentage difference may be 20%.

Processing circuitry of patient monitoring system 2 may determine, based at least in part on the difference 39 in nociception parameter levels, whether a nociception has occurred during interrogation window 35. To make such a determination, processing circuitry of patient monitoring system 2 may compare the difference 39 in nociception parameter levels with a threshold value, such as a threshold difference value. For example, if processing circuitry of patient monitoring system 2 determines that the difference 39 in nociception parameter level is greater than or equal to the threshold difference value, processing circuitry of patient monitoring system 2 may determine an occurrence of the nociception event during interrogation window 35. This threshold difference value can be stored in memory 41 (FIG. 3) of processing circuitry of patient monitoring system 2 or a memory of another device.

In some examples, in operation, e.g., during a medical procedure, processing circuitry of patient monitoring system 2 may continuously and/or periodically (e.g., every second, every 15 seconds, every 30 seconds, etc.) determine baseline nociception parameter level 36 and nociception parameter level 38 as processing circuitry of patient monitoring system 2 monitors the nociception parameter 32 of patient 6 via nociception monitor 4. At a given point in time, interrogation window 35 used to determine nociception parameter level 38 may be an interrogation window that has just ended at the given point in time. Thus, for example, given an interrogation window 35 of 10 seconds, then, at a given point in time, interrogation window 35 may be the preceding 10 seconds of the given point in time.

Given interrogation window 35, processing circuitry of patient monitoring system 2 may determine the baseline window 33 that corresponds to interrogation window 35. For example, given baseline window 33 of 30 seconds and an interrogation window 35 of 20 seconds, where there is a 10 second gap between the end of baseline window 33 and interrogation window 35, processing circuitry of patient monitoring system 2, at a point in time of monitoring nociception parameter 32 of patient 6, may determine nociception parameter level 38 based on the values of nociception parameter 32 in interrogation window 35 that started 20 seconds ago and has just ended, and may determine baseline nociception parameter level 36 based on the values of nociception parameter 32 in baseline window 33 that started 60 seconds ago and ended 30 seconds ago. Processing circuitry of patient monitoring system 2 may therefore determine the difference 39 in nociception parameter levels between baseline nociception parameter level 36 and nociception parameter level 38 to determine whether a nociception event has occurred.

In this way, as shown in FIG. 2F, processing circuitry of patient monitoring system 2 may continuously determine the difference 39 in nociception parameter levels over time by continuously determine baseline nociception parameter level 36 and nociception parameter level 38 as processing circuitry of patient monitoring system 2 monitors the nociception parameter 32 of patient 6 via nociception monitor 4. When difference 39 in nociception parameter levels is greater than or equal to a threshold difference value ($T_{DNP}$) 37, such at times t11 and t12, processing circuitry of patient monitoring system 2 may determine that a nociception event has occurred at times t11 and t12.

Processing circuitry of patient monitoring system 2 may, in response to determining an occurrence of a nociception event for patient 6, provide an indication of the nociception event, such as by generating and presenting an alert via display 16 or another output device including output circuitry. In some examples, processing circuitry of patient monitoring system 2 may, in response to determining an occurrence of a nociception event for patient 6, provide an indication to adjust an amount of analgesic to administer to patient 6 via display or another output device including output circuitry. Thus, in these examples, if processing circuitry of patient monitoring system 2 determines that a difference 39 in a nociception parameter level is greater than or equal to a threshold difference value ($T_{DNP}$) 37, then processing circuitry of patient monitoring system 2 may provide an indication to adjust an amount of analgesic to administer to patient 6, such as by providing an indication to increase the amount of analgesic to administer to patient 6.

In some examples, a clinician may manually control analgesic administration device 18 to administer analgesic to patient 6. As such, in order to provide an indication to adjust an amount of analgesic to administer to patient 6, processing circuitry of patient monitoring system 2 may output, for display at display 16, an indication to a clinician to adjust the amount of analgesic administered to patient 6. For example, processing circuitry of patient monitoring system 2 may output, for display at display 16, an indication of the amount of analgesic to administer to patient 6 or a more general instruction or suggestion to the clinician to increase or otherwise adjust the amount of analgesic.

In some examples, processing circuitry of patient monitoring system 2 may be able to control analgesic administration device 18 to administer analgesic to patient 6 without user intervention. As such, in order to provide an indication to adjust an amount of analgesic to administer to patient 6, processing circuitry of patient monitoring system 2 may output a signal to analgesic administration device 18 to direct analgesic administration device 18 to increase or otherwise adjust the amount of analgesic to administer to patient 6. Analgesic administration device 18 may, in response to receiving the signal, increase or otherwise adjust the amount of analgesic to administer to patient 6.

In some examples, processing circuitry of patient monitoring system 2 may determine how much to adjust the amount of analgesic administered to patient 6 and/or whether to adjust the amount of analgesic administered to patient 6 based on the current level of analgesic administered to patient 6 and/or the total amount of analgesic administered to patient 6 during the current medical procedure. In some examples, processing circuitry of patient monitoring system 2 may limit the amount of analgesic administered to patient 6 at any point in time to a specified analgesic level. As such, processing circuitry of patient monitoring system 2 may increase the amount of analgesic administered to patient 6 at a point in time to no more than the specified analgesic level. If processing circuitry of patient monitoring system 2 determines that increasing the amount of analgesic administered to patient 6 would cause the amount of analgesic administered to patient 6 to rise above the specified analgesic level, then processing circuitry of patient monitoring system 2 may refrain from increasing the amount of analgesic administered to patient 6 or providing an instruction to increase the amount of analgesic via display 16.

In some examples, processing circuitry of patient monitoring system 2 may determine how much to adjust the amount of analgesic administered to patient 6 and/or whether to adjust the amount of analgesic administered to patient 6 based on the total amount of analgesic administered to patient 6 during the course of the surgery or other medical procedure. For example, the total amount of analgesic administered to patient 6 over the course of the surgery may not exceed a total analgesic limit. If processing circuitry of patient monitoring system 2 determines that increasing the amount of analgesic administered to patient 6 would cause the total amount of analgesic administered to patient 6 over the course of the surgery to rise above the total analgesic limit, then processing circuitry of patient monitoring system 2 may refrain from increasing the amount of analgesic administered to patient 6 providing an instruction to increase the amount of analgesic via display 16. Processing circuitry of patient monitoring system 2 may determine how much to increase the amount of analgesic administered to patient 6 using any techniques described above alone or in combination with each other.

The techniques described herein may provide one or more advantages. By determining whether a nociception event has occurred based on identifying distinct changes in the nociception event instead of relying only on comparison of a nociception parameter to a nociception threshold value, patient monitoring system 2 may be able to determine that a nociception event has occurred even if the nociception parameter of patient 6 does not exceed a nociception threshold, thereby enabling patient monitoring system 2 to more accurately detect the occurrence of nociception events.

Being able to more accurately detect the occurrence of nociception events may enable patient monitoring system 2 to better administer (e.g., more timely) the proper amount of analgesic to patient 6. The proper amount of analgesic can be, for example, an amount of analgesic necessary to provide the desired analgesia outcomes for patient 6 but not being too much analgesic, which may lead to undesirable outcomes for patient 6. Administering a more proper amount of analgesic to the patient (e.g., better corresponding to surgical stress experienced by patient 6 during surgery using the techniques described herein may have one or more beneficial outcomes, such as leading to reductions in opioid administration during and after surgery, post-operative pain scores, the length of the hospital stay, and/or post-operative complications.

Figure 3:
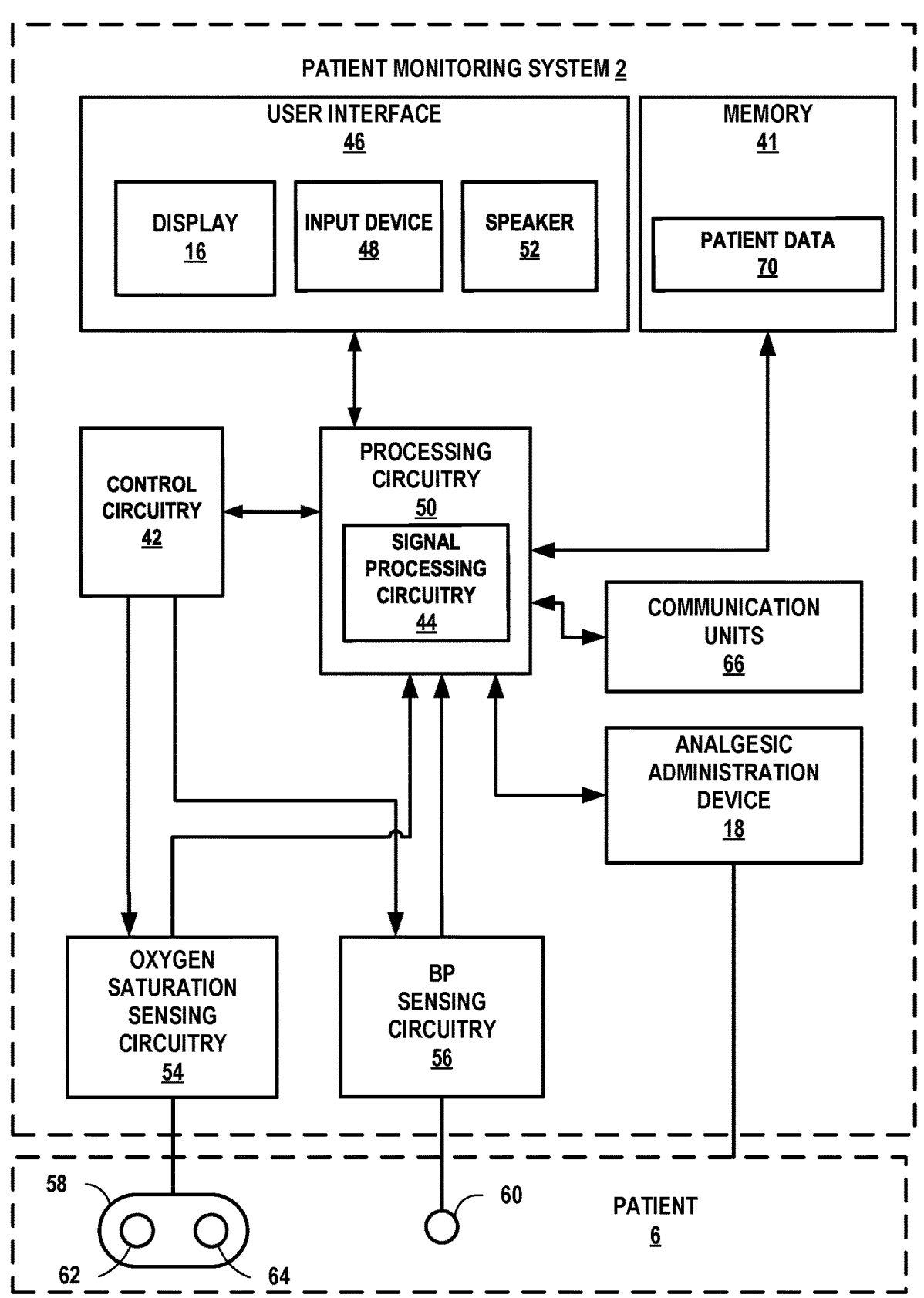
FIG. 3 is a block diagram illustrating the patient monitoring system of FIG. 1.

FIG. 3 is a block diagram illustrating an example of the patient monitoring system 2 of FIG. 1. As shown in FIG. 3, in some examples, patient monitoring system 2 includes analgesic administration device 18, memory 41, control circuitry 42, user interface 46, processing circuitry 50, sensing circuitry 54 and 56, sensing devices 58 and 60, and one or more communication units 66. In the example shown in FIG. 1, user interface 46 may include display 16, input device 48, and/or speaker 52, which may be any suitable audio device including circuitry configured to generate and output a sound and/or noise. In some examples, patient monitoring system 2 may be configured to determine and output (e.g., for display at display 16) the nociception parameter of a patient 6 during a medical procedure.

Processing circuitry 50, as well as other processors, processing circuitry, controllers, control circuitry, and the like, described herein, may include one or more processors. Processing circuitry 50 and control circuitry 42 may each include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 50 and/or control circuitry 42 may include multiple components, such as any combination of one or more microprocessors, one or more DSPs, one or more ASICs, or one or more FPGAs, as well as other discrete or integrated logic circuitry, and/or analog circuitry.

Control circuitry 42 may be operatively coupled to processing circuitry 50. Control circuitry 42 is configured to control an operation of sensing devices 58 and 60. In some examples, control circuitry 42 may be configured to provide timing control signals to coordinate operation of sensing devices 58 and 60. For example, sensing circuitry 54 and 56 may receive from control circuitry 42 one or more timing control signals, which may be used by sensing circuitry 54 and 56 to turn on and off respective sensing devices 58 and 60, such as to periodically collect calibration data using sensing devices 58 and 60. In some examples, processing circuitry 50 may use the timing control signals to operate synchronously with sensing circuitry 54 and 56. For example, processing circuitry 50 may synchronize the operation of an analog-to-digital converter and a demultiplexer with sensing circuitry 54 and 56 based on the timing control signals.

One or more communication units 66 include circuitry operable to communicate with one or more devices external to patient monitoring system 2 via one or more networks by transmitting and/or receiving network signals on the one or more networks such as the Internet, a Wide Area Network, a Local Area Network, and the like. Examples of one or more communication units 66 include a network interface card (e.g. such as an Ethernet card), an optical transceiver, a radio frequency transceiver, or any other type of device that can send and/or receive information. Other examples of one or more communication units 66 may include Near-Field Communications (NFC) units, Bluetooth® radios, short wave radios, cellular data radios, wireless network (e.g., Wi-Fi®) radios, as well as universal serial bus (USB) controllers.

Memory 41 may be configured to store, for example, patient data 70. For example, processing circuitry 50 may store various data associated with patient 6 in patient data 70. For example, processing circuitry 50 may store the nociception parameter of patient 6, a nociception threshold, a threshold difference value, the total amount of analgesic administered to patient 6, a current level of analgesic being administered to patient 6, and the like in patient data 70 in memory 41. The nociception threshold can be specific to patient 6 or used for a population of patients.

In some examples, memory 41 may store program instructions. The program instructions may include one or more program modules that are executable by processing circuitry 50. When executed by processing circuitry 50, such program instructions may cause processing circuitry 50 to provide the functionality ascribed to it herein. The program instructions may be embodied in software, firmware, and/or RAMware. Memory 41 may include any one or more of volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

User interface 46 may include a display 16, an input device 48, and a speaker 52. In some examples, user interface 46 may include fewer or additional components. User interface 46 is configured to present information to a user (e.g., a clinician). For example, user interface 46 and/or display 16 may include a monitor, cathode ray tube display, a flat panel display such as a liquid crystal (LCD) display, a plasma display, a light emitting diode (LED) display, and/or any other suitable display. In some examples, user interface 46 may be part of a multiparameter monitor (MPM) or other physiological signal monitor used in a clinical or other setting, a personal digital assistant, mobile phone, tablet computer, laptop computer, any other suitable computing device, or any combination thereof, with a built-in display or a separate display.

In some examples, processing circuitry 50 may be configured to present, by user interface 46, such as display 16, a graphical user interface to a user. The graphical user interface can include information regarding the delivery of analgesic or anesthesia to patient 6, one or more sensed nociception parameters, indications of regions of interest in the nociception parameter, and the like. For example, the graphical user interface may include time graph 30 of FIGS. 2A-2F of the nociception parameter of patient 6 over time, the regions of interest of the nociception parameter of patient 6, and indications of occurrences of nociception events. In some examples, the graphical user interface can also include an instruction or suggestion to a clinician to administer additional analgesics or anesthesia or otherwise adjust the delivery of analgesics, anesthesia, or other pharmaceutical agents or fluids. User interface 46 may also include means for projecting audio to a user, such as speaker 52.

In some examples, processing circuitry 50 may also receive input signals from additional sources (not shown), such as a user. For example, processing circuitry 50 may receive from input device 48, such as a keyboard, a mouse, a touch screen, buttons, switches, a microphone, a joystick, a touch pad, or any other suitable input device or combination of input devices, an input signal. The input signal may contain information about patient 6, such as physiological parameters, treatments provided to patient 6, or the like. Additional input signals may be used by processing circuitry 50 in any of the determinations or operations it performs in accordance with examples described herein. For example, the input processing circuitry 50 receives via input device 48 can indicate the occurrence of a medical event, based on which processing circuitry 50 may determine a patient-specific nociception threshold.

In some examples, processing circuitry 50 and user interface 46 may be part of the same device or supported within one housing (e.g., a computer or monitor). In other examples, processing circuitry 50 and user interface 46 may be separate devices configured to communicate through a wired connection or a wireless connection.

Sensing circuitry 54 and 56 is configured to receive signals ("physiological signals") indicative of physiological parameters from respective sensing devices 58 and 60 and communicate the physiological signals to processing circuitry 50. Sensing devices 58 and may include any sensing hardware configured to sense a physiological parameter of a patient, e.g., indicative of a nociception response of patient 6. Example sensing hardware includes, but is not limited to, one or more electrodes, light sources, optical receivers, blood pressure cuffs, or the like. The sensed physiological signals may include signals indicative of physiological parameters from a patient, such as, but not limited to, blood pressure, blood oxygen saturation (e.g., pulse oximetry and/or regional oxygen saturation), blood volume, heart rate, heart rate variability, skin conductance, and respiration. For example, sensing circuitry 54 and 56 may include, but are not limited to, blood pressure sensing circuitry, blood oxygen saturation sensing circuitry, blood volume sensing circuitry, heart rate sensing circuitry, temperature sensing circuitry, electrocardiography (ECG) sensing circuitry, electroencephalogram (EEG) sensing circuitry, electromyogram (EMG) sensing circuitry or any combination thereof.

In some examples, sensing circuitry 54 and 56 and/or processing circuitry 50 may include signal processing circuitry 44 configured to perform any suitable analog conditioning of the sensed physiological signals. For example, sensing circuitry 54 and 56 may communicate to processing circuitry 50 an unaltered (e.g., raw) signal. Processing circuitry e.g., signal processing circuitry 44, may be configured to modify a raw signal to a usable signal by, for example, filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof.

In some examples, the conditioned analog signals may be processed by an analog-to-digital converter of signal processing circuitry 44 to convert the conditioned analog signals into digital signals. In some examples, signal processing circuitry 44 may operate on the analog or digital form of the signals to separate out different components of the signals. In some examples, signal processing circuitry 44 may perform any suitable digital conditioning of the converted digital signals, such as low pass, high pass, band pass, notch, averaging, or any other suitable filtering, amplifying, performing an operation on the signal, performing any other suitable digital conditioning, or any combination thereof. In some examples, signal processing circuitry 44 may decrease the number of samples in the digital detector signals. In some examples, signal processing circuitry 44 may remove dark or ambient contributions to the received signal. Additionally, or alternatively, sensing circuitry 54 and 56 may include signal processing circuitry 44 to modify one or more raw signals and communicate to processing circuitry 50 one or more modified signals.

In the example shown in FIG. 3, patient monitoring system 2 includes an oxygen saturation sensing device 58 (also referred to herein as blood oxygen saturation sensing device 58), which is configured to generate an oxygen saturation signal indicative of blood oxygen saturation within the venous, arterial, and/or capillary systems within a region of patient 6. For example, oxygen saturation sensing device 58 may include a sensor configured to non-invasively generate a plethysmography (PPG) signal. One example of such a sensor may be one or more oximetry sensors (e.g., one or more pulse oximetry sensors) placed at one or multiple locations on patient 6, such as at a fingertip of patient 6, an earlobe of patient 6, and the like.

In some examples, oxygen saturation sensing device 58 may be configured to be placed on the skin of patient 6 to determine regional oxygen saturation of a particular tissue region, e.g., the frontal cortex or another cerebral location of patient 6. Oxygen saturation sensing device 58 may include emitter 62 and detector 64. Emitter 62 may include at least two light emitting diodes (LEDs), each configured to emit at different wavelengths of light, e.g., red or near infrared light. As used herein, the term "light" may refer to energy produced by radiative sources and may include any wavelength within one or more of the ultrasound, radio, microwave, millimeter wave, infrared, visible, ultraviolet, gamma ray or X-ray electromagnetic radiation spectra. In some examples, light drive circuitry (e.g., within sensing device 58, sensing circuitry 54, control circuitry 42, and/or processing circuitry 50) may provide a light drive signal to drive emitter 62 and to cause emitter 62 to emit light. In some examples, the LEDs of emitter 62 emit light in the range of about 600 nanometers (nm) to about 1000 nm. In a particular example, one LED of emitter 62 is configured to emit light at about 730 nm and the other LED of emitter 62 is configured to emit light at about 810 nm. Other wavelengths of light may be used in other examples.

Detector 64 may include a first detection element positioned relatively "close" (e.g., proximal) to emitter 62 and a second detection element positioned relatively "far" (e.g., distal) from emitter 62. In some examples, the first detection elements and the second detection elements may be chosen to be specifically sensitive to the chosen targeted energy spectrum of emitter 62. Light intensity of multiple wavelengths may be received at both the "close" and the "far" detector 64. For example, if two wavelengths are used, the two wavelengths may be contrasted at each location and the resulting signals may be contrasted to arrive at an oxygen saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). In operation, light may enter detector 64 after passing through the tissue of patient 6, including skin, bone, other shallow tissue (e.g., non-cerebral tissue and shallow cerebral tissue), and/or deep tissue (e.g., deep cerebral tissue). Detector 64 may convert the intensity of the received light into an electrical signal. The light intensity may be directly related to the absorbance and/or reflectance of light in the tissue. Surface data from the skin and skull may be subtracted out, to generate an oxygen saturation signal for the target tissues over time.

Oxygen saturation sensing device 58 may provide the oxygen saturation signal to processing circuitry 50. Additional example details of determining oxygen saturation based on light signals may be found in commonly assigned U.S. Pat. No. 9,861,317, which issued on Jan. 9, 2018, and is entitled "Methods and Systems for Determining Regional Blood Oxygen Saturation." One example of such an oxygen saturation signal may be a plethysmography (PPG) signal.

In the example shown in FIG. 3, patient monitoring system 2 includes a blood pressure sensing device 60, which is configured to generate a blood pressure signal indicative of a blood pressure of patient 6. For example, blood pressure sensing device 60 may include a blood pressure cuff configured to non-invasively sense blood pressure or an arterial line configured to invasively monitoring blood pressure in an artery of patient 6. In some examples, the blood pressure signal may include at least a portion of a waveform of the acquisition blood pressure. Blood pressure sensing device 60 may be configured to generate a blood pressure signal indicative of the blood pressure of patient over time. Blood pressure sensing device 60 may provide the blood pressure signal to sensing circuitry 56, processing circuitry 50, or to any other suitable processing device, which may be part of patient monitoring system 2 or a device separate from patient monitoring system 2, such as another device co-located with patient monitoring system 2 or remotely located relative to patient monitoring system 2.

In operation, blood pressure sensing device 60 and oxygen saturation sensing device 58 may each be placed on the same or different parts of the body of patient 6. For example, blood pressure sensing device 60 and oxygen saturation sensing device 58 may be physically separate from each other and may be separately placed on patient 6. As another example, blood pressure sensing device 60 and oxygen saturation sensing device 58 may in some cases be supported by a single sensor housing. One or both of blood pressure sensing device 60 or oxygen saturation sensing device 58 may be further configured to measure other patient parameters, such as hemoglobin, respiratory rate, respiratory effort, heart rate, saturation pattern detection, response to stimulus such as bispectral index (BIS) or electromyography (EMG) response to electrical stimulus, or the like. While an example patient monitoring system 2 is shown in FIG. 3, the components illustrated in FIG. 3 are not intended to be limiting. Additional or alternative components and/or implementations may be used in other examples.

Processing circuitry 50 may be configured to receive one or more physiological signals generated by sensing devices 58 and 60 and sensing circuitry 54 and 56. The physiological signals may include a signal indicating blood pressure and/or a signal, such as a PPG signal, indicating oxygen saturation. Processing circuitry 50 may be configured to obtain the nociception parameter for patient 6 over time while patient 6 is in a medical procedure by continuously determining, based on the one or more physiological signals generated by sensing devices 58 and 60, the nociception parameter for patient 6. For example, the nociception parameter may be a value between 0 to 100 that indicates the amount of surgical stress experienced by patient 6 during the medical procedure. As processing circuitry 50 receives the one or more physiological signals during surgery of patient 6, processing circuitry 50 may be able to periodically or continuously determine, based on the one or more physiological signals, the nociception parameter for patient 6 over time. As such processing circuitry 50, sensing circuitry 54 and 56, and sensing devices 58 and 60 may together implement nociception monitor 4 of patient monitoring system 2 shown in FIG. 1. In other examples, processing circuitry 50 may be configured to obtain the nociception parameter for patient 6 via one or more external devices. For example, processing circuitry 50 may be configured to communicate, via communication units 66, with an external device that sends the nociception parameter for patient 6 to processing circuitry 50.

In accordance with aspects of the present disclosure, processing circuitry 50 is configured to monitor the nociception parameter of patient 6 over time and to determine one or more regions of interest in the nociception parameter of patient 6. When processing circuitry 50 determines a region of interest in the nociception parameter of patient 6, processing circuitry 50 may be configured to output an indication of the region of interest, such as for display at display 16.

Processing circuitry 50 may be configured to determine regions of interest in the nociception parameter as regions that correspond to distinct changes in nociception parameter over time, such as a distinct rise in nociception parameter over time or a distinct dip in nociception parameter 32. In some examples, processing circuitry 50 may be configured to determine the regions of interest as regions in the nociception parameter that corresponds to the leading edges of the distinct changes in the nociception parameter. In some examples, processing circuitry 50 may be configured to determine the regions of interest as regions in the nociception parameter that encompass an initial distinct change from an initial value until nociception parameter 32 returns to the initial value.

In accordance with aspects of the present disclosure, processing circuitry 50 is also configured to monitor the nociception parameter of patient 6 over time and to determine the occurrence of nociception events based at least in part on comparing a nociception parameter level to a baseline nociception parameter level. Processing circuitry 50 may be configured to, at a given point in time, determine a nociception parameter level based on values of the nociception parameter in an interrogation window 35 (FIG. 2E) immediately prior to the given point in time, such as the peak nociception parameter value in the interrogation window. Processing circuitry 50 may also be configured to determine a baseline nociception parameter level based on values of the nociception parameter in a baseline window 33 (FIG. 2E) corresponding to the interrogation window, such as an average of the nociception parameter values in the baseline window, where the baseline window ends prior to the start of the interrogation window.

Processing circuitry 50 may be configured to determine a difference in nociception parameter levels between the nociception parameter level and the baseline nociception parameter level, such as by subtracting the nociception parameter level and the baseline nociception parameter level. Processing circuitry 50 may be configured to compare the difference in nociception parameter levels with a threshold difference value. If processing circuitry 50 determines that the difference in nociception parameter levels is greater than or equal to the threshold difference value, then processing circuitry 50 may be configured to determine that a nociception event has occurred at the given point in time.

In some examples, processing circuitry 50 may, in response to determining that the nociception event has occurred, output a notification via user interface 46. The notification can be any suitable visual, audible, somatosensory, or any combination thereof, notification that indicates the nociception event was detected. In some examples, the notification includes an indication to adjust an amount of analgesic to administer to patient 6. That is, processing circuitry 50 may cause analgesic administration device 18 to increase the amount of analgesic administered to patient 6 to dampen the surgical stress experienced by patient 6 by directly controlling analgesic administration device 18 or by generating a notification that causes a clinician to control analgesic administration device 18. Example analgesics that analgesic administration device 18 can administer include, but are not limited to, one or more of remifentanil, alfentanil, and fentanyl.

In some examples, to provide an indication to adjust an amount of analgesic to administer to patient 6, processing circuitry 50 may output, for display at display 16, an indication to increase an amount of analgesic to administer to patient 6, so that a clinician that views display 16 may therefore control analgesic administration device 18 to adjust the amount of analgesic administered to patient 6.

In some examples, to provide an indication to adjust an amount of analgesic to administer to patient 6, processing circuitry 50 may send, to analgesic administration device 18, the indication to adjust the amount of analgesic administered to patient 6. Analgesic administration device 18 may, in response to receiving the indication, adjust the amount of analgesic that analgesic administration device 18 delivers to patient 6. In this way, patient monitoring system 2 may act as an automated analgesic administration system.

In some examples, processing circuitry 50 may determine how much to adjust the amount of analgesic administered to patient 6 based on at least one of: a current amount of analgesic being administered to patient 6 and a total amount of analgesic administered to patient 6 during surgery. In some examples, it may be desirable to control the amount of analgesic being administered to patient 6 so that the amount at any point in time does not exceed a specified analgesic level. Thus, processing circuitry 50 may determine whether increasing the current amount of analgesic administered to patient 6 may cause the amount of analgesic administered to exceed the specified analgesic level and, if so, to reduce the increase in the amount of analgesic administered to patient 6 so that the amount of analgesic administered to patient 6 remains below the specified analgesic level.

In some examples, it may be desirable to limit to the total amount of analgesic administered to patient 6 during surgery. Thus, in some examples, processing circuitry 50 may determine whether increasing the current amount of analgesic administered to patient 6 may cause the total amount of analgesic administered to patient 6 during surgery to exceed the limit and, if so, to reduce the increase in the amount of analgesic administered to patient 6 so that the amount of analgesic administered to patient 6 does not cause the total amount of analgesic administered to patient 6 during surgery to exceed the limit.

The components of patient monitoring system 2 that are shown and described as separate components are shown and described as such for illustrative purposes only. In some examples the functionality of some of the components may be combined in a single component. For example, the functionality of processing circuitry 50 and control circuitry 42 may be combined in a single processor system. Additionally, in some examples the functionality of some of the components of patient monitoring system 2 shown and described herein may be divided over multiple components or over multiple devices. For example, some or all of the functionality of control circuitry 42 may be performed in processing circuitry 50, or sensing circuitry 54 and 56. In other examples, the functionality of one or more of the components may be performed in a different order or may not be required.

FIG. 4 is a flow diagram illustrating an example method of determining a patient-specific nociception threshold. Although FIG. 4 is described with respect to processing circuitry 50 of patient monitoring system 2 (FIGS. 1 and 3), in other examples, different processing circuitry, alone or in combination with processing circuitry 50, may perform any part of the technique of FIG. 4.

As shown in FIG. 4, processing circuitry 50 may monitor nociception parameters of a patient 6 during a medical procedure (402). Processing circuitry 50 may determine, based at least in part on the nociception parameter of the patient 6 in an interrogation window 35 (FIG. 2E), a nociception parameter level (404). Processing circuitry 50 may determine, based at least in part on the nociception parameter of the patient 6 in a baseline window 33 (FIG. 2E) that corresponds to the interrogation window 35, a baseline nociception parameter level (406). Processing circuitry 50 may determine a difference in nociception parameter levels between the baseline nociception parameter level and the nociception parameter level (408). Processing circuitry 50 may detect, based at least in part on the difference in nociception parameter levels, an occurrence of a nociception event (410). Processing circuitry 50 may, in response to detecting the occurrence of the nociception event, provide an indication to adjust an amount of analgesic administered to the patient 6 (412).

In some examples, to detect, based at least in part on the difference in nociception parameter levels, the occurrence of the nociception event, processing circuitry 50 determines whether the difference in nociception parameter levels is greater than or equal to a threshold value and, in response to determining that the difference in nociception parameter levels is greater than or equal to the threshold value, determine the occurrence of the nociception event.

In some examples, the difference in nociception parameter values between the baseline nociception parameter level and the nociception parameter level is one of: an absolute difference or a percentage difference.

In some examples, to determine, based at least in part on the nociception parameter in the baseline window, the baseline nociception parameter level, processing circuitry 50 determines the baseline nociception parameter level as one of: an average of values of the nociception parameter within the baseline window 33 or a weighted average of values of the nociception parameter within the baseline window 33.

In some examples, to determine, based at least in part on the nociception parameter level in the interrogation window 35, the nociception parameter level, processing circuitry 50 determines the nociception parameter level as one of: a maximum nociception parameter value, a minimum nociception parameter value, or a percentile nociception parameter value of values of the nociception parameter within the interrogation window 35.

In some examples, baseline window 33 has a first duration, interrogation window 35 has a second duration, and baseline window 33 precedes interrogation window 35. In some examples, processing circuitry 50 may further identify, one or more distinct changes of the nociception parameter over time and determine one or more regions of interest in the nociception parameter based at least in part on the one or more distinct changes. In some examples, the interrogation window 35 is within one of the one or more regions of interest. In some examples, the processing circuitry 50 may output an indication of the one or more regions of interest in the nociception parameter.

In some examples, to identify the one or more distinct changes of the nociception parameter over time, processing circuitry 50 identifies one or more distinct rises in the nociception parameter over time. In some examples, to determine the one or more regions of interest in the nociception parameter, processing circuitry 50 determines the one or more regions of interest in the nociception parameter that corresponds to the one or more distinct rises in the nociception parameter over time.

In some examples, to identify the one or more distinct changes of the nociception parameter over time, processing circuitry 50 identifies one or more distinct dips in the nociception parameter over time. In some examples, to determine the one or more regions of interest in the nociception parameter, processing circuitry 50 determines the one or more regions of interest in the nociception parameter that corresponds to the one or more distinct dips in the nociception parameter over time.

In some examples, to identify the one or more distinct changes of the nociception parameter over time, processing circuitry 50 identifies one or more regions in the nociception parameter that each encompasses a leading edge of a distinct rise in the nociception parameter over time.

In some examples, to identify the one or more distinct changes of the nociception parameter over time, processing circuitry 50 identifies one or more regions in the nociception parameter that each encompasses a leading edge of a distinct dip in the nociception parameter over time.

In some examples, to identify the one or more distinct changes of the nociception parameter over time, processing circuitry 50 identifies one or more regions in the nociception parameter that each encompasses a distinct rise in the nociception parameter over time from an initial value of the nociception parameter until a return from the distinct rise in the nociception parameter to the initial value.

In some examples, to identify the one or more distinct changes of the nociception parameter over time, processing circuitry 50 identifies one or more regions in the nociception parameter that each encompasses a distinct dip in the nociception parameter over time from an initial value of the nociception parameter until a return from the distinct dip in the nociception parameter to the initial value.

The following examples may illustrate one or more aspects of the disclosure.

Example 1: A method includes monitoring, by processing circuitry, a nociception parameter of a patient during a medical procedure; determining, by the processing circuitry and based at least in part on the nociception parameter of the patient in an interrogation window, a nociception parameter level; determining, by the processing circuitry and based at least in part on the nociception parameter of the patient in a baseline window that corresponds to the interrogation window, a baseline nociception parameter level; determining, by the processing circuitry, a difference in nociception parameter levels between the baseline nociception parameter level and the nociception parameter level; detecting, by the processing circuitry and based at least in part on the difference in nociception parameter levels, an occurrence of a nociception event; and in response to detecting the occurrence of the nociception event, providing, by the processing circuitry, an indication to adjust an amount of analgesic administered to the patient.

Example 2: The method of example 1, wherein detecting, based at least in part on the difference in nociception parameter levels, the occurrence of the nociception event comprises: determining, by the processing circuitry, whether the difference in nociception parameter levels is greater than or equal to a threshold value; and in response to determining that the difference in nociception parameter levels is greater than or equal to the threshold value, determining, by the processing circuitry, the occurrence of the nociception event.

Example 3: The method of any of examples 1 or 2, wherein the difference in nociception parameter values between the baseline nociception parameter level and the nociception parameter level is one of: an absolute difference or a percentage difference.

Example 4: The method of any of examples 1-3, wherein determining, based at least in part on the nociception parameter in the baseline window, the baseline nociception parameter level comprises: determining, by the processing circuitry, the baseline nociception parameter level as one of: an average of values of the nociception parameter within the baseline window or a weighted average of values of the nociception parameter within the baseline window.

Example 5: The method of any of examples 1-4 wherein determining, based at least in part on the nociception parameter level in the interrogation window, the nociception parameter level comprises: determining, by the processing circuitry, the nociception parameter level as one of: a maximum nociception parameter value, a minimum nociception parameter value, or a percentile nociception parameter value of values of the nociception parameter within the interrogation window.

Example 6: The method of any of examples 1-5, wherein: the baseline window has a first duration; the interrogation window has a second duration; and the baseline window precedes the interrogation window.

Example 7: The method of any of examples 1-6, further includes identifying, by processing circuitry, one or more distinct changes of the nociception parameter over time; and determining, by the processing circuitry, one or more regions of interest in the nociception parameter based at least in part on the one or more distinct changes.

Example 8: The method of example 7, wherein the interrogation window is within one of the one or more regions of interest.

Example 9: The method of any of examples 7 or 8, further includes outputting, by the processing circuitry, an indication of the one or more regions of interest in the nociception parameter.

Example 10: The method of any of examples 7-9, wherein identifying the one or more distinct changes of the nociception parameter over time further comprises: identifying, by the processing circuitry, one or more distinct rises in the nociception parameter over time.

Example 11: The method of example 10, wherein determining the one or more regions of interest in the nociception parameter further comprises: determining, by the processing circuitry, the one or more regions of interest in the nociception parameter that corresponds to the one or more distinct rises in the nociception parameter over time.

Example 12: The method of any of examples 7-9, wherein identifying the one or more distinct changes of the nociception parameter over time further comprises: identifying, by the processing circuitry, one or more distinct dips in the nociception parameter over time.

Example 13: The method of example 12, wherein determining the one or more regions of interest in the nociception parameter further comprises: determining, by the processing circuitry, the one or more regions of interest in the nociception parameter that corresponds to the one or more distinct dips in the nociception parameter over time.

Example 14: The method of any of examples 7-9, wherein identifying the one or more distinct changes of the nociception parameter over time further comprises: identifying, by the processing circuitry, one or more regions in the nociception parameter that each encompasses a leading edge of a distinct rise in the nociception parameter over time.

Example 15: The method of any of examples 7-9, wherein identifying the one or more distinct changes of the nociception parameter over time further comprises: identifying, by the processing circuitry, one or more regions in the nociception parameter that each encompasses a leading edge of a distinct dip in the nociception parameter over time.

Example 16: The method of any of examples 7-9, wherein identifying the one or more distinct changes of the nociception parameter over time further comprises: identifying, by the processing circuitry, one or more regions in the nociception parameter that each encompasses a distinct rise in the nociception parameter over time from an initial value of the nociception parameter until a return from the distinct rise in the nociception parameter to the initial value.

Example 17: The method of any of examples 7-9, wherein identifying the one or more distinct changes of the nociception parameter over time further comprises: identifying, by the processing circuitry, one or more regions in the nociception parameter that each encompasses a distinct dip in the nociception parameter over time from an initial value of the nociception parameter until a return from the distinct dip in the nociception parameter to the initial value.

Example 18: A system includes memory; and processing circuitry configured to perform any combination of the method of Examples 1-17.

Example 19: The system of example 18, further comprising sensing circuitry configured to sense the nociception parameter of the patient.

Example 20: The system of any of examples 18 or 19, further comprising an output device configured to output the indication to adjust the amount of analgesic administered to the patient.

Example 21: A non-transitory computer readable storage medium comprising instructions that, when executed, cause processing circuitry to perform any combination of the method of examples 1-17.

The techniques described in this disclosure, including those attributed to patient monitoring system 2, processing circuitry 50, control circuitry 42, sensing circuitries 54, 56, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices. Processing circuitry, control circuitry, and sensing circuitry, as well as other processors and controllers described herein, may be implemented at least in part as, or include, one or more executable applications, application modules, libraries, classes, methods, objects, routines, subroutines, firmware, and/or embedded code, for example.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. The computer-readable medium may be an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

The functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements.

What is claimed is:

1. A system comprising:
memory configured to store a threshold rate of change of a nociception parameter; and
processing circuitry communicably coupled to the memory and configured to:
monitor the nociception parameter of a patient during a medical procedure comprising administration of analgesic to the patient;
provide a continuous measure of the nociception parameter over time during the medical procedure;
determine a rate of change of the nociception parameter and compare the rate of change to the threshold rate of change;
determine a change in the nociception parameter based on the rate of change crossing the threshold rate of change;
identify a region of interest in the nociception parameter based on the determined change;

detect an occurrence of a nociception event in the region of interest; and in response to detecting the occurrence of the nociception event, provide an indication to adjust an amount of the analgesic administered to the patient.

2. The system of claim 1, wherein the threshold rate of change comprises a threshold rate of increase, and wherein the change in the nociception parameter comprises the rate of change exceeding the threshold rate of increase.

3. The system of claim 1, wherein the processing circuitry is further configured to:

establish an interrogation window within the region of interest, determine a maximum nociception parameter value within the interrogation window, and detect the occurrence of the nociception event based on the maximum nociception parameter value.

4. The system of claim 3, wherein the processing circuitry is further configured to establish a baseline value of the nociception parameter over a baseline window, wherein:

the baseline window has a first duration;

the interrogation window has a second duration; and the baseline window precedes the interrogation window.

5. The system of claim 3, wherein the region of interest comprises a leading edge of the determined change in the nociception parameter.

6. The system of claim 1, further comprising a user interface, wherein the processing circuitry is further configured to:

output, via the user interface, an indication of the region of interest in the nociception parameter.

7. The system of claim 5, wherein the leading edge comprises the leading edge of a rise in the nociception parameter.

8. The system of claim 5, wherein the leading edge comprises the leading edge of a dip in the nociception parameter.

9. The system of claim 7, wherein the region of interest encompasses a period of time from the rise in the nociception parameter from an initial value of the nociception parameter until a return to the initial value.

10. The system of claim 8, wherein the region of interest encompasses a period of time from the dip in the nociception parameter from an initial value of the nociception parameter until a return to the initial value.

11. A method comprising:

monitoring, by processing circuitry, a nociception parameter of a patient during a medical procedure comprising administration of an analgesic to the patient;

providing a continuous measure of the nociception parameter over time during the medical procedure;

determining a rate of change of the nociception parameter and comparing the rate of change to a threshold rate of change of the nociception parameter;

determining, by the processing circuitry, a change in the nociception parameter based on the rate of change crossing the threshold rate of change;

identifying a region of interest in the nociception parameter based on the determined change;

detecting, by the processing circuitry, an occurrence of a nociception event in the region of interest; and in response to detecting the occurrence of the nociception event, providing, by the processing circuitry, an indication to adjust an amount of the analgesic administered to the patient.

12. The method of claim 11, wherein identifying the region of interest comprises identifying a leading edge of the change in the nociception parameter.

13. The method of claim 11, further comprising establishing a baseline value of the nociception parameter in a baseline window preceding the region of interest, and wherein detecting the occurrence of the nociception event comprises comparing the nociception parameter in the region of interest to the baseline value.

14. The method of claim 11, further comprising adjusting, by the processing circuitry, the amount of the analgesic administered to the patient.

\* \* \* \* \*